(12) United States Patent
Hlasta

(10) Patent No.: US 6,297,242 B1
(45) Date of Patent: Oct. 2, 2001

(54) N-SUBSTITUTED AMIDINE AND GUANIDINE OXAZOLIDINONE ANTIBACTERIALS AND METHODS OF USE THEREOF

(75) Inventor: Dennis Hlasta, Doylestown, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/621,819

(22) Filed: Jul. 21, 2000

Related U.S. Application Data

(60) Provisional application No. 60/148,469, filed on Aug. 12, 1999.

(51) Int. Cl.⁷ ................... A61K 31/5377; A61K 31/541; C07D 413/10; C07D 417/10
(52) U.S. Cl. ................... 514/236.8; 514/254.02; 514/376; 514/227.8; 544/60; 544/137; 544/369; 548/229
(58) Field of Search ............... 514/227.8, 236.8, 514/254.02, 376; 544/60, 137, 369; 548/229

(56) References Cited

U.S. PATENT DOCUMENTS

| | | |
|---|---|---|
| 5,565,571 | 10/1996 | Barbachyn et al. . |
| 5,654,428 | 8/1997 | Barbachyn et al. . |
| 5,792,765 | 8/1998 | Riedl et al. . |
| 5,827,857 | 10/1998 | Riedl et al. . |
| 5,837,870 | 11/1998 | Pearlman et al. . |
| 5,883,093 | 3/1999 | Hutchinson et al. . |
| 5,910,504 | 6/1999 | Hutchinson . |
| 5,929,248 | 7/1999 | Barbachyn et al. . |
| 6,069,141 * | 5/2000 | Barbachyn et al. ............... 514/236.8 |
| 6,090,820 | 7/2000 | Barbachyn et al. . |
| 6,124,334 | 9/2000 | Hutchinson . |

FOREIGN PATENT DOCUMENTS

| | | |
|---|---|---|
| WO 93/09103 | 10/1992 | (EP) . |
| WO 95/07271 | 8/1994 | (EP) . |
| WO 96/23788 | 1/1996 | (EP) . |
| WO 98/54161 | 5/1998 | (EP) . |
| 11-322729 | 3/1999 | (JP) . |

OTHER PUBLICATIONS

R.W. Johnson Pharmaceutical Research Institute Chemical/Patent Search Report dated Feb. 8, 1999 Report No. 99–016; Novelty: 5–Acetylaminomethyl–3–[3–Fluoro–4–(Isoindolyl) Phenyl]–2–Oxazolidinones.

\* cited by examiner

*Primary Examiner*—Joseph K. McKane
*Assistant Examiner*—Sonya Wright
(74) *Attorney, Agent, or Firm*—Kenneth J. Dow

(57) ABSTRACT

N-substituted amidine and guanidine oxazolidinone compounds of the formula:

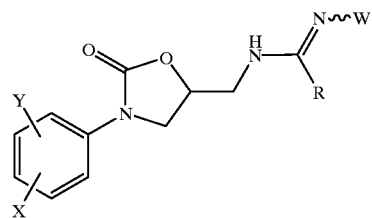

in which the substituents have the meaning indicated in the description. These compounds are useful as antibacterial agents.

15 Claims, No Drawings

N-SUBSTITUTED AMIDINE AND GUANIDINE OXAZOLIDINONE ANTIBACTERIALS AND METHODS OF USE THEREOF

CROSS REFERENCE TO RELATED APPLICATION

This application claims the benefit of U.S. Provisional Application No. 60/148,469, filed Aug. 12, 1999, the contents of which are hereby incorporated by reference.

FIELD OF THE INVENTION

The present invention relates to the field of phenyl oxazolidinone compounds having antibacterial activity, pharmaceutical compositions containing the compounds, and methods of treating bacterial infections with the compounds.

BACKGROUND OF THE INVENTION

Oxazolidinones have been identified, within the last twenty years, as a new class of antibacterials which are active against numerous multidrug-resistant gram positive organisms. Particularly problematic pathogens include methicillin-resistant *Staphylococcus aureus* (MRSA), vancomycin-resistant enterococci (VRE) and penicillin- and cephalosporin-resistant *Streptococcus pneumoniae*. As a class oxazolidinones exhibit a unique mechanism of action. Studies have shown that these compounds selectively bind to the 50S ribosomal subunit and inhibit bacterial translation at the initiation phase of protein synthesis. Examplary members of oxazolidinones are linezolid (see WO 95/07271) and eperezolid.

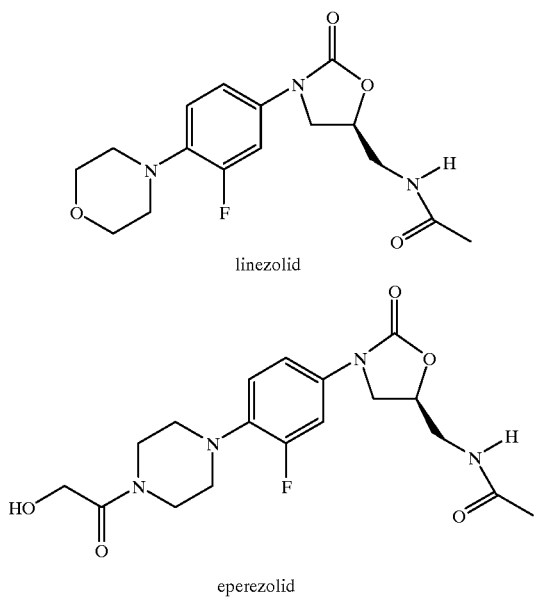

linezolid eperezolid

U.S. Pat. No. 5,792,765 to Riedl et al. discloses a series of substituted oxazolidinones (cyanoguanidine, cyanoamidines, and amidines) useful as antibacterial medicaments.

U.S. Pat. No. 5,910,504 to Hutchinson discloses a series of heteroaromatic ring substituted phenyl oxazolidinones.

WO 98/54161 (Hester et al.) discloses amides, thioamides, ureas, and thioureas which are antibacterial agents.

WO 95/07271 (Barbachyn et al.) oxazine and thiazine oxazolidinone derivatives such as linezolid and its analogs which are useful antimicrobial agents, effective against a number of human and veterinary pathogens, including gram-positive aerobic bacteria such as multiply-resistant staphylococci, streptococci and enterococci as well as anaerobic organisms such as Bacteroides spp. and Clostridia spp. species, and acid-fast organisms such as *Mycobacterium tuberculosis, Mycobacterium avium* and Mycobacterium spp.

SUMMARY OF THE INVENTION

The invention provides new oxazolidinone compounds of the formula I:

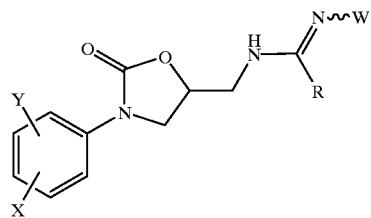

wherein:
R is H, alkyl, $OR_1$, $SR_1$, amino, $NHR_1$, $NR_1R_2$, ($C_1$–$C_8$) alkylaryl or mono-, di-, tri-, and per- halo-($C_1$–$C_8$) alkyl;

W is H, CN, $COR_1$, $COOR_1$, $CONHR_1$, CO—$NR_1R_2$, $SO_2R_1$, $SO_2NHR_1$, $SO_2$—$NR_1R_2$, or $NO_2$, $R_1$ and $R_2$ are independently selected from H, alkyl aryl, or, in the case of any —$NR_1R_2$ group $R_1$ and $R_2$ taken together with the nitrogen group may form a cyclic amino derivative:

X is selected from H, CN, $COR_1$, $COOR_1$, $CONHR_1$, CO—$NR_1R_2$, $SOR_1$, $SO_2R_1$, $SO_2NHR_1$, $SO_2$—$NR_1R_2$, $NO_2$, ($C_1$–$C_8$) alkyl, $OR_1$, $SR_1$, amino, $NHR_1$, $NR_1R_2$, aryl, ($C_1$–$C_8$) alkylaryl (such as benzyl), and (mono-, di-, tri-, and per-) halo-alkyl and heteroaryl;

Y is 0 to 4 members independently selected from the group consisting of H, halogen, OH, mercapto, nitro, halo-$C_{1-8}$-alkyl, $C_{1-8}$ alkoxyl, thio-$C_{1-8}$-alkyl, $C_{1-8}$ alkyl-amino, di($C_{1-8}$-alkyl-)amino, formyl, carboxy, alkoxycarbonyl, $C_{1-8}$ alkyl-CO—O—, $C_{1-8}$ alkyl-CO—NH—, carboxamide, aryl, substituted-aryl, heteroaryl, substituted-heteroaryl, CN, amine, alkoxy, NHCO—($C_{1-8}$ alkyl), $C_{3-6}$ cycloalkyl, $C_{1-8}$ alkyl optionally substituted with one or more members selected from the group consisting of F, Cl, OH, $C_{1-8}$ alkoxyl and $C_{1-8}$ acyloxy; and optical isomers, enantiomers, diastereomers, racemates and racemic mixtures thereof, or pharmaceutically acceptable salts and esters thereof.

Compounds of the above formula are useful as antibacterial agents for the treatment of bacterial infections in humans and animals.

The present invention is also directed to a method of treating a subject having a condition caused by or contributed to by bacterial infection, which comprises administering to said subject a therapeutically effective amount of the compound of Formula I.

The present invention is further directed to a method of preventing a subject from suffering from a condition caused by or contributed to by bacterial infection, which comprises administering to the subject a prophylactically effective dose of the pharmaceutical composition of a compound of Formula I.

Other objects and advantages will become apparent to those skilled in the art from a review of the ensuing specification.

DETAILED DESCRIPTION

Relative to the above description, certain definitions apply as follows.

Unless specified otherwise, the terms "alkyl", "alkenyl", and "alkynyl" may be normal or branched groups with 1–8 carbon atoms.

Aryl is a carbocyclic aromatic radical including, but not limited to, phenyl, 1- or 2-naphthyl and the like. The aromatic radical may be substituted by independent replacement of 1 to 3 of the hydrogen atoms thereon with halogen, OH, CN, mercapto, nitro, amino, alkyl, O-alkyl, S-alkyl, NH-alkyl, N(alkyl)$_2$, (mono-, di-, tri-, and per-) halo-alkyl, formyl, COR$_1$, COOR$_1$, CONHR$_1$, CO—NR$_1$R$_2$, SOR$_1$, SO$_2$R$_1$, SO$_2$NHR$_1$, SO$_2$—NR$_1$R$_2$, alkyl-CO—O—, alkyl-CO—NH—, or carboxamide or a second aryl group. Illustrative aryl radicals include, for example, phenyl, naphthyl, diphenyl, fluorophenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, tolyl, xylyl, dimethylcarbamylphenyl and the like.

The term "halo" or "halogen" means fluoro, chloro, bromo and iodo. (Mono-, di-, tri-, and per-) halo-alkyl is an alkyl radical substituted by independent replacement of the hydrogen atoms thereon with halogen.

Heteroaryl refers to a cyclic aromatic radical having from five to ten ring atoms of which one ring atom is selected from S, O, and N; 0–2 ring atoms are additional heteroatoms independently selected from S, O, and N; and the remaining ring atoms are carbon, the radical being joined to the rest of the molecule via any of the ring atoms, such as, for example, pyridinyl, pyrazinyl, pyrimidinyl, pyrroyl, pyrazolyl, imidazolyl, thiazolyl, oxazolyl, isoxazolyl, thiadiazolyl, triazolyl, oxadiazolyl, thienyl, furanyl, quinolinyl, isoquinolinyl, and the like. The heteroaryl group may be substituted by independent replacement of 1 to 3 of the hydrogen atoms thereon with halogen, OH, CN, mercapto, nitro, amino, alkyl, O-alkyl, S-alkyl, NH-alkyl, N(alkyl)$_2$, (mono-, di-, tri-, and per-) halo-alkyl, formyl, COR$_1$, COOR$_1$, CONHR$_1$, CO—NR$_1$R$_2$, SOR$_1$, SO$_2$R$_1$, SO$_2$NHR$_1$, SO$_2$—NR$_1$R$_2$, alkyl-CO—O—, alkyl-CO—NH—, or carboxamide. Heteroaryl may be substituted with a mono-oxo to give for example a 4-oxo-1H-quinoline.

A cyclic amino group is a 4 to 8 membered nitrogen containing cyclic group where the other remaining members are selected from carbon, nitrogen, oxygen or sulfur, for instance an azetidinyl group, pyrrolidinyl group, piperidinyl group, morpholino group, piperazinyl, or groups of the following formulae:

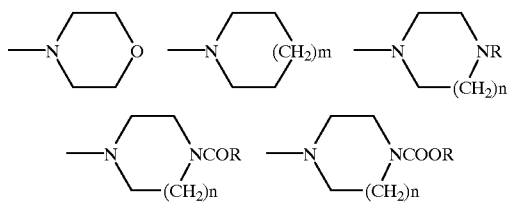

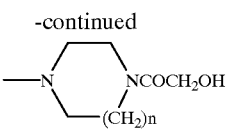

wherein m is −2 to 4 and n is 1–4;

The compounds of the instant invention are asymmetric in the oxazolidinone ring at the 5-position and thus exist as optical antipodes. As such, all possible optical antipodes, enantiomers or diastereomers resulting from additional asymmetric centers that may exist in optical antipodes, racemates and racemic mixtures thereof are also part of this invention. The antipodes can be separated by methods known to those skilled in the art such as, for example, fractional recrystallization of diastereomeric salts of enantiomerically pure acids. Alternatively, the antipodes can be separated by chromatography on a Pirkle column.

The phrase "pharmaceutically acceptable salts" denotes salts of the free base which possess the desired pharmacological activity of the free base and which are neither biologically nor otherwise undesirable. These salts may be derived from inorganic or organic acids. Examples of inorganic acids are hydrochloric acid, nitric acid, hydrobromic acid, sulfuric acid, or phosphoric acid. Examples of organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicyclic acid and the like. Suitable salts are furthermore those of inorganic or organic bases, such as KOH, NaOH, Ca(OH)$_2$, Al(OH)$_3$, piperidine, morpholine, ethylamine, triethylamine and the like.

Also included within the scope of the invention are the hydrated forms of the compounds which contain various amounts of water, for instance, the hydrate, hemihydrate and sesquihydrate forms.

The term "subject" includes, without limitation, any animal or artificially modified animal. In the preferred embodiment, the subject is a human.

The term "drug-resistant" or "drug-resistance" refers to the characteristics of a microbe to survive in presence of a currently available antimicrobial agent such as an antibiotic at its routine, effective concentration.

The compounds described in the present invention possess antibacterial activity due to their novel structure, and are useful as antibacterial agents for the treatment of bacterial infections in humans and animals. Compounds of Formula I which are most preferred for such purposes are those in which X is any of the following:

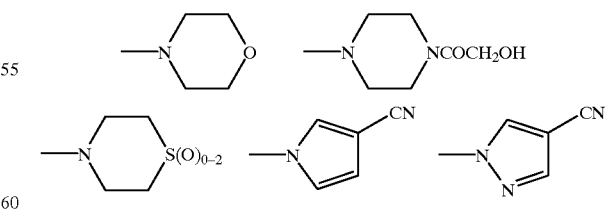

Preferred groups for W are CN and COR$_1$. In one embodiment, W is selected from COR$_1$, COOR$_1$, CONHR$_1$, CO—NR$_1$R$_2$.

The compounds of Formula I that are the subject of this invention may be prepared from readily available starting materials such as known oxazolidinone intermediates in accordance with synthetic methods well known in the art. The following are representative procedures outlined in Schemes I and II:
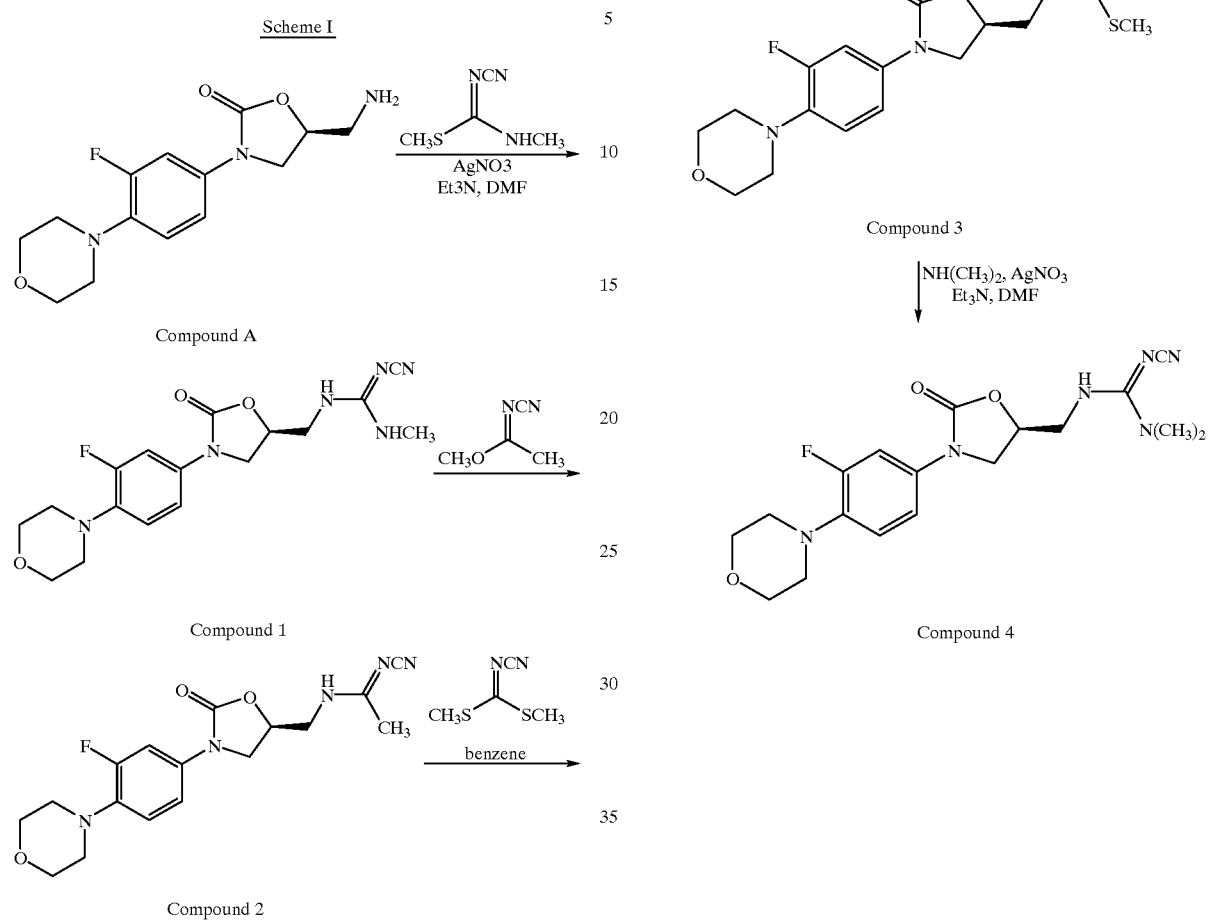
Scheme I
Compound A
Compound 1
Compound 2
Compound 3
Compound 4
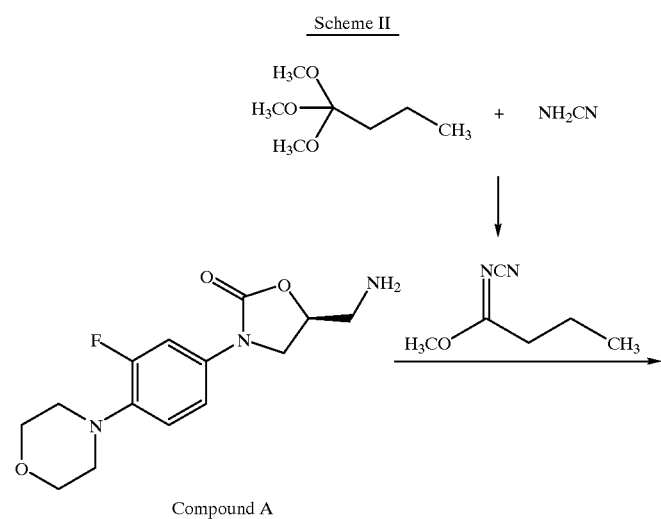
Scheme II
Compound A

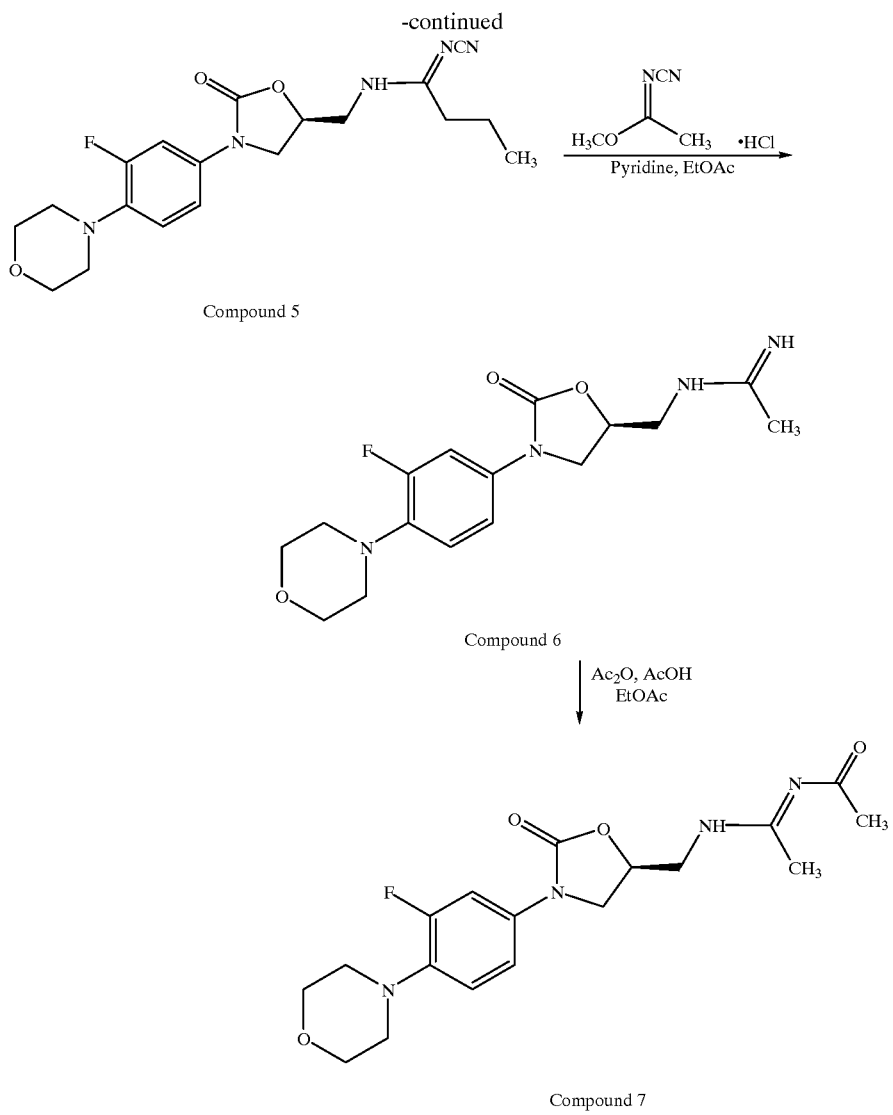

In accordance with Scheme I, Compound A prepared by methods disclosed in International Patent application WO 95/07271, hereby incorporated by references, is reacted with N-Cyano-N',S-dimethylisothiourea in the presence of AgNO$_3$, Et$_3$N and DMF to produce Compound 1. Compound A is reacted with methyl N-cyanoacetimidate in THF, and the product is Compound 2. Reaction of Compound A with dimethyl N-cyanodithioiminocarbonate gives Compound 3. Compound 3 is further reacted with dimethylamine in the presence of silver nitrate, Et$_3$N, and DMF to produce Compound 4.

In accordance with Scheme II, Compound A is reacted with methyl N-cyanobutyrimidate in MeOH, and the product is Compound 5. N-cyanobutyrimidate is readily obtained through reaction of commercially available trimethyl orthobutyrate with cyanamide. Reaction of Compound A with methyl acetimidate hydrochloride and pyridine in ethyl acetate gives compound 6. Compound 6 is further reacted with acetic anhydride and catalytic acetic acid in ethyl acetate to produce Compound 7.

These compounds have antimicrobial activity against susceptible and drug resistant *S. aureus, S. epidermidis, S. pneumoniae, S. pyogenes, E. faecalis, E faecium, Moraxella catarrhalis* and *H. influenzae*. These compounds are particularly useful against drug resistant Gram positive cocci such as methicillin-resistant staphylococci and vancomycin-resistant enterococci. These compounds are useful in the treatment of community-acquired pneumonia, upper and lower respiratory tract infections, skin and soft tissue infections, hospital-acquired lung infections, bone and joint infections, and other bacterial infections.

Minimal inhibitory concentration (MIC) has been an indicator of in vitro antibacterial activity widely used in the art. The in vitro antimicrobial activity of the compounds was determined by the microdilution broth method following the test method from the National Committee for Laboratory Standards (NCCLS). This method is described in the NCCLS Document M7-A4, Vol.17, No.2, "Methods for Dilution Antimicrobial Susceptibility Test for Bacteria that Grow Aerobically-Fourth Edition", which is incorporated herein by reference.

In this method two-fold serial dilutions of drug in cation adjusted Mueller-Hinton broth are added to wells in microdilution trays. The test organisms are prepared by adjusting the turbidity of actively growing broth cultures so that the final concentration of test organism after it is added to the wells is approximately $5 \times 10^4$ CFU/well.

Following inoculation of the microdilution trays, the trays are incubated at 35° C. for 16–20 hours and then read. The MIC is the lowest concentration of test compound that completely inhibits growth of the test organism. The amount of growth in the wells containing the test compound is compared with the amount of growth in the growth-control wells (no test compound) used in each tray. As set forth in Table 1, compounds of the present invention were tested against a variety of Gram positive and Gram negative pathogenic bacteria resulting in a range of activities, from 1 to $\geq 128$ μg/mL depending on the organism tested.

TABLE 1

| | NCCLS Broth Microdilution method MIC (μg/mL) | | | | | | |
|---|---|---|---|---|---|---|---|
| organism | Cmpd 1 | Cmpd 2 | Cmpd 3 | Cmpd 4 | Cmpd 5 | Cmpd 6 | Cmpd 7 |
| E. faecium OC3312 | 32 | 2 | 8 | 64 | 8 | >128 | 64 |
| MRSA OC2878 | 32 | 1 | 4 | 32 | 8 | 128 | 16 |
| S. aureus OC4172 | 16 | 2 | 4 | 16 | 8 | >128 | 32 |

This invention further provides a method of treating bacterial infections, or enhancing or potentiating the activity of other antibacterial agents, in warm-blooded animals, which comprises administering to the animals a compound of the invention alone or in admixture with another antibacterial agent in the form of a medicament according to the invention.

When the compounds are employed for the above utility, they may be combined with one or more pharmaceutically acceptable carriers, e.g., solvents, diluents, and the like, and may be administered orally in such forms as tablets, capsules, dispersible powders, granules, or suspensions containing for example, from about 0.5% to 5% of suspending agent, syrups containing, for example, from about 10% to 50% of sugar, and elixirs containing, for example, from about 20% to 50% ethanol, and the like, or parenterally in the form of sterile injectable solutions or suspensions containing from about 0.5% to 5% suspending agent in an isotonic medium. These pharmaceutical preparations may contain, for example, from about 0.5% up to about 90% of the active ingredient in combination with the carrier, more usually between 5% and 60% by weight.

Compositions for topical application may take the form of liquids, creams or gels, containing a therapeutically effective concentration of a compound of the invention admixed with a dermatologically acceptable carrier.

In preparing the compositions in oral dosage form, any of the usual pharmaceutical media may be employed. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred. These active compounds may also be administered parenterally or intraperitoneally. Solutions or suspensions of these active compounds as a free base or pharmacological acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The effective dosage of active ingredient employed may vary depending on the particular compound employed, the mode of administration and the severity of the condition being treated. However, in general, satisfactory results are obtained when the compounds of the invention are administered at a daily dosage of from about 0.1 mg/kg to about 400 mg/kg of animal body weight, preferably given in divided doses two to four times a day, or in sustained release form. For most large mammals the total daily dosage is from about 0.07 g to 7.0 g, preferably from about 100 mg to 1000 mg. Dosage forms suitable for internal use comprise from about 100 mg to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The production of the above-mentioned pharmaceutical compositions and medicaments is carried out by any method known in the art, for example, by mixing the active ingredients(s) with the diluent(s) to form a pharmaceutical composition (e.g. a granulate) and then forming the composition into the medicament (e.g. tablets).

The following examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

EXAMPLE 1

N-Cyano-N'-[[(5S)-3-[3-fluoro-4-(4-morpholinyl)phenyl]-2-oxo-5-oxazolidinyl]methyl]-N"-methylguanidine Compound 1

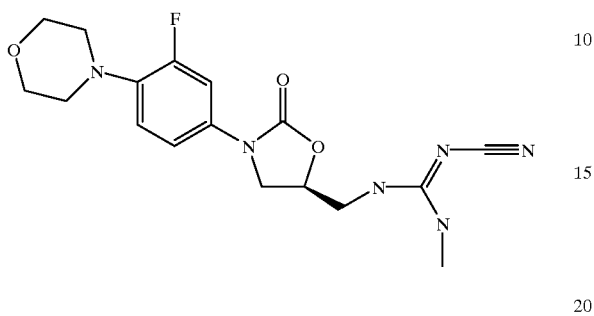

A mixture of 296 mg of Compound A, 129 mg of N-Cyano-N',S-dimethylisothiourea, and 170 mg of silver nitrate in 10 mL of DMF containing 10 drops of triethylamine was stirred at room temperature for 2 hours. The reaction mixture was filtered, diluted with water and extracted with ethyl acetate. The extracts were dried over magnesium sulfate, filtered, and concentrated to give a yellow oil. Trituration with ether gave 59 mg of II as off-white crystals, m.p. 186–188° C. MS (Cl) MH+377.

EXAMPLE 2

N-Cyano-N'-[[(5S)-3-[3-fluoro-4-(4-morpholinyl)phenyl]-2-oxo-5-oxazolidinyl]methyl]ethanimidamide Compound 2

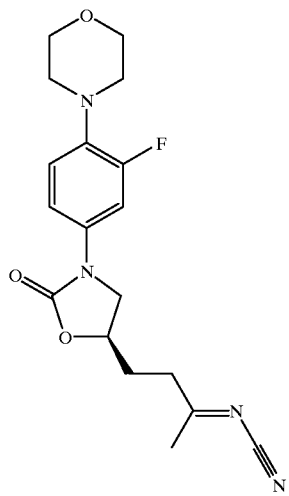

A mixture of 200 mg of Methyl N-cyanoacetimidate and 580 mg of Compound A in 3 mL of THF was refluxed for 1.5 hours. An addition 3 mL of THF was added and the mixture was filtered while hot. The crystalline product was washed with ether and dried to give 290 mg of Compound 2 as white crystals, m.p. 193–196° C. MS (Cl) MH+362.

EXAMPLE 3

N-Cyano-N'-[[(5S)-3-[3-fluoro-4-(4-morpholinyl)phenyl]-2-oxo-5-oxazolidinyl]methyl]carbamimidothioic acid, methyl ester Compound 3

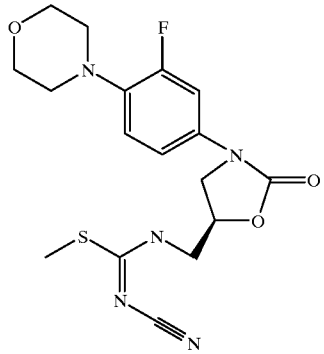

A mixture of 295 mg of Compound A and 146 mg of dimethyl N-cyanodithioiminocarbonate in 13 mL of benzene was refluxed for 4 hours. After cooling, filtration gave 200 mg of Compound 3, m.p. 206–208. MS (Cl) MH+394.

EXAMPLE 4

N-Cyano-N'-[[(5S)-3-[3-fluoro-4-(4-morpholinyl)phenyl]-2-oxo-5-oxazolidinyl]methyl]-N", N"-dimethylguanidine Compound 4

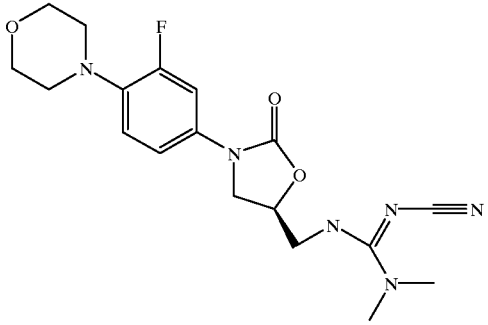

To a solution of 160 mg of Compound 3 and 100 mg of silver nitrate in 10 mL of DMF was added 0.5 mL of 40% aqueous dimethylamine. After stirring at room temperature of 1 hour, the mixture was filtered and concentrated to give an oil. The oil was dissolved in ethyl acetate and washed with water (5×), dried over MgSO$_4$, filtered and concentrated. The residue oil was triturated with ether to give 19 mg of V as white crystals, m.p. 180–181. MS (Cl) MH+391.

EXAMPLE 5

N-Cyano-N'-[[(5S)-3-[3-fluoro-4-(4-morpholinyl)phenyl]-2-oxo-5-oxazolidinyl]methyl]butyrimidate Compound 5

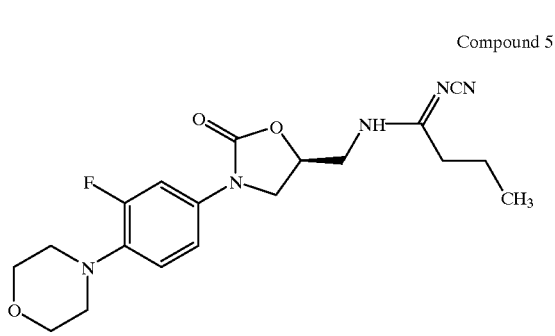

a) Synthesis of N-cyanobutyrimidate

To a solution of 1.48 g of trimethyl orthobutyrate in 10 ml of benzene was added 420 mg of cyanamide and the mixture was heated to reflux temperature for 12 hours. The solvent was removed in vacuo and the residue subjected to silica gel chromatography with ethyl ether as eluent to afford N-cyanobutyrimidate as a colorless oil.

b) Synthesis of N-Cyano-N'-[[(5S)-3-[3-fluoro-4-(4-morpholinyl)phenyl]-2-oxo-5-oxazolidinyl]methyl] butyrimidate A mixture of 126 mg of methyl N-cyanoacetimidate and 295 mg of Compound A in 2 mL of MeOH was refluxed for 3 hours. The solution was concentrated in vacuo and the residue subjected to silica gel chromatography with acetone as eluent. Removal of solvent gave Compound 5 as white crystals, m.p. 137–138° C. Anal. Calcd. for: C19H24FN5O3: C, 58.60; H, 6.21; N, 17.98. Found: C, 58.36; H, 6.10; N, 17.79.

EXAMPLE 6

N-[[(5S)-3-[3-fluoro-4-(4-morpholinyl)phenyl]-2-oxo-5-oxazolidinyl]methyl]acetimidate Compound 6

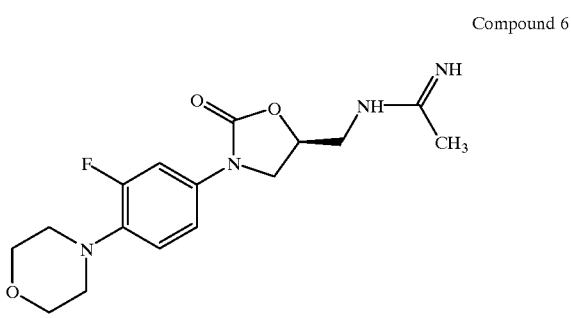

A mixture of 110 mg of methyl acetimidate hydrochloride, 237 mg of pyridine, and 297 mg of Compound A in 2 mL of ethyl acetate was stirred at room temperature for 12 hours. An additional 1 mL of ethyl acetate was added and the mixture stirred an additional 24 hours. The precipitate was filtered to afford 297 mg of Compound 6. MS (Cl) MH+337.

EXAMPLE 7

N-Acetyl-N'-[[(5S)-3-[3-fluoro-4-(4-morpholinyl)phenyl]-2-oxo-5-oxazolidinyl]methyl]acetimidate Compound 7

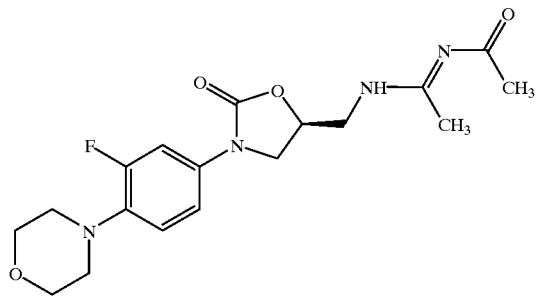

A solution of 300 mg of Compound 6, 0.3 mL of acetic anhydride, 1 drop of acetic acid, and 1.0 mL of ethyl acetate was warmed at 60° C. for 3 days. The mixture was diluted with an additional 1 mL of ethyl acetate, cooled, and filtered to afford crude Compound 7. The crude solid was purified by silica gel chromatography with ethyl acetate as eluent. The resulting oil was triturated with ethyl ether to give 22 mg of Compound 7 as a solid, m.p. 130–132° C. MS (Cl) MH+379.

The invention has been described in detail with particular reference to the above embodiments thereof. The above embodiments and examples are given to illustrate the scope and spirit of the present invention. These embodiments and examples will make apparent, to those skilled in the art, other embodiments and examples. These other embodiments and examples are within the contemplation of the present invention. It will be understood that variations and modifications can be effected within the spirit and scope of the invention; therefore, the instant invention should be limited only by the appended claims.

What is claimed is:

1. A compound of Formula I:

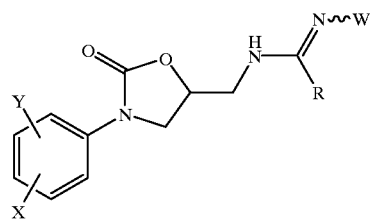

Formula I wherein

R is H, alkyl, cycloalkyl, $OR_1$, $SR_1$, amino, $NHR_1$, $NR_1R_2$, $C_1$–$C_8$ alkylaryl, or mono-, di-, tri- or per-halo-$C_1$–$C_8$ alkyl;

W is H, CN, $COR_1$, $COOR_1$, $CONHR_1$, CO—$NR_1R_2$, $SO_2R_2$, $SO_2NHR_1$, $SO_2$—$NR_1R_2$, or $NO_2$;

$R_1$ and $R_2$ are independently H, alkyl, or mono-, di-, tri- or per-halo-$C_1$–$C_8$ alkyl, or, in the case of —$NR_1R_2$, $R_1$ and $R_2$ taken together with the nitrogen may be a cyclic amino derivative;

X is H, CN, $COR_1$, $COOR_1$, $CONHR_1$, CO—$NR_1R_2$, $SOR_1$, $SO_2R_1$, $SO_2NHR_1$, $SO_2$—$NR_1R_2$, $NO_2$, $C_1$–$C_8$ alkyl, $OR_1$, $SR_1$, amino, $NHR_1$, $NR_1R_2$, $C_1$–$C_8$ alkylaryl, halogen, halo-alkyl, alkoxy, heteroaryl, or aryl; and Y is 0 to 4 members independently selected from the group consisting of H, halogen, OH, mercapto, nitro, halo-$C_{1-8}$-alkyl, $C_{1-8}$ alkoxyl, thio-$C_{1-8}$-alkyl, $C_{1-8}$ alkyl-amino, di($C_{1-8}$-alkyl-)amino, formyl, carboxy, alkoxycarbonyl, $C_{1-8}$ alkyl-CO—O—, $C_{1-8}$ alkyl-CO—NH—, carboxamide, aryl, substituted-aryl, heteroaryl, substituted-heteroaryl, CN, amine, alkoxy, NHCO—($C_{1-8}$ alkyl), $C_{3-6}$ cycloalkyl, $C_{1-8}$ alkyl optionally substituted with one or more members selected from the group consisting of F, Cl, OH, $C_{1-8}$ alkoxyl and $C_{1-8}$ acyloxy;

and optical isomers, enantiomers, diastereomers, racemates and racemic mixtures thereof, or pharmaceutically acceptable salts thereof.

2. The compound of claim 1 wherein X is selected from the group consisting of

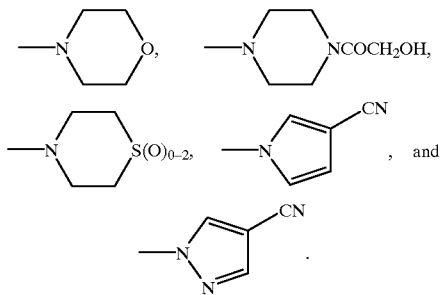

3. The compound of claim 2 wherein R is $CH_3$ and W is CN.

4. The compound of claim 2 wherein W is selected from $COR_1$, $COOR_1$, $CONHR_1$, and CO—$NR_1R_2$.

5. The compound of claim 1 wherein R is a cyclic amino group selected from:

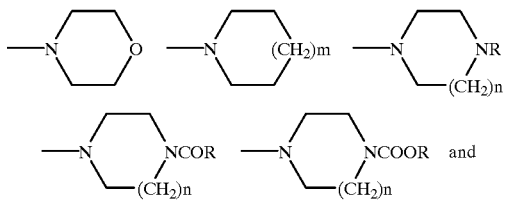

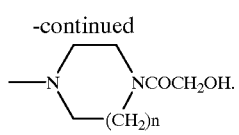

6. A compound of claim 1 selected from the group consisting of: N-Cyano-N'-[[(5S)-3-[3-fluoro-4-(4-morpholinyl)phenyl]-2-oxo-5-oxazolidinyl]methyl]-N"-methylguanidine, and its pharmaceutically acceptable salts.

7. A compound of claim 1 selected from the group consisting of: N-Cyano-N'-[[(5S)-3-[3-fluoro-4-(4-morpholinyl)phenyl]-2-oxo-5-oxazolidinyl]methyl]-N", N"-dimethylguanidine, and its pharmaceutically acceptable salts.

8. A compound of claim 1 selected from the group consisting of: N-Cyano-N'-[[(5S)-3-[3-fluoro-4-(4-morpholinyl)phenyl]-2-oxo-5-oxazolidinyl]methyl] carbamimidothioic acid, methyl ester, and its pharmaceutically acceptable salts.

9. A compound of claim 1 selected from the group consisting of: N-Cyano-N'-[[(5S)-3-[3-fluoro-4-(4-morpholinyl)phenyl]-2-oxo-5-oxazolidinyl]methyl] ethanimidamide, and its pharmaceutically acceptable salts.

10. A pharmaceutical composition comprising a compound of claim 1 and a pharmaceutically acceptable carrier.

11. A method of treating a subject having a condition caused by or contributed to by bacterial infection, which comprises administering to said subject a therapeutically effective amount of the compound of Formula I.

12. The method of claim 11 wherein said condition is selected from the group consisting of community-acquired pneumonia, upper and lower respiratory tract infections, skin and soft tissue infections, bone and joint infections, and hospital-acquired lung infections.

13. The method of claim 11 wherein said bacterial infection is caused by a bacterium selected from the group consisting of *S. aureus, S. epidermidis, S. pneumoniae, S. pyogenes,* Enterococcus spp., *Moraxella catarrhalis* and *H. influenzae.*

14. The method of claim 11 wherein said bacterial infection is caused by a Gram-positive coccus bacterium.

15. The method of claim 14 wherein said Gram-positive coccus is antibiotic-resistant.

* * * * *